United States Patent [19]
Brosnahan, III

[11] Patent Number: 5,645,598
[45] Date of Patent: Jul. 8, 1997

[54] SPINAL FUSION DEVICE WITH POROUS MATERIAL

[75] Inventor: Robert E. Brosnahan, III, Germantown, Tenn.

[73] Assignee: Smith & Nephew, Inc., Memphis, Tenn.

[21] Appl. No.: 631,135

[22] Filed: Apr. 15, 1996

Related U.S. Application Data

[63] Continuation-in-part of Ser. No. 585,526, Jan. 16, 1996.

[51] Int. Cl.$^6$ ........................................ A61F 2/44
[52] U.S. Cl. ................................ 623/17; 606/61
[58] Field of Search ........................... 623/16, 17, 18; 606/61

[56] References Cited

U.S. PATENT DOCUMENTS

| | | | |
|---|---|---|---|
| 4,501,269 | 2/1985 | Bagby | 623/17 |
| 4,834,757 | 5/1989 | Brantigan | 623/17 |
| 4,878,915 | 11/1989 | Brantigan | 623/17 |
| 4,936,848 | 6/1990 | Bagby . | |
| 4,961,740 | 10/1990 | Ray et al. . | |
| 5,015,247 | 5/1991 | Michelson | 623/17 |
| 5,026,373 | 6/1991 | Ray et al. . | |
| 5,055,104 | 10/1991 | Ray . | |
| 5,147,402 | 9/1992 | Bohler et al. . | |
| 5,192,327 | 3/1993 | Brantigan | 623/17 |
| 5,397,364 | 3/1995 | Kozak et al. . | |
| 5,423,816 | 6/1995 | Lin . | |
| 5,425,772 | 6/1995 | Brantigan | 623/17 |
| 5,458,638 | 10/1995 | Kuslich et al. | 623/17 |
| 5,489,308 | 2/1996 | Kuslich et al. | 623/17 |

FOREIGN PATENT DOCUMENTS

| | | |
|---|---|---|
| 0577178 | 1/1994 | European Pat. Off. ............... 623/17 |
| 0599419 | 6/1994 | European Pat. Off. ............... 623/17 |
| 26 28 443 | 12/1976 | Germany . |
| 8707827 | 12/1987 | WIPO ................................... 623/17 |
| 9106261 | 5/1991 | WIPO ................................... 623/17 |

*Primary Examiner*—Debra S. Brittingham
*Attorney, Agent, or Firm*—Pravel, Hewitt, Kimball & Krieger

[57] ABSTRACT

An implant for insertion into at least one bore formed between opposing vertebrae of a spine where the vertebrae are separated by a space and each vertebrae has end plates. The implant is in the shape of a solid generally cylindrical body having a first and a second end, an outer surface, opposing sides and a longitudinal axis. The body has threads on a portion of the outer surface between the first and second ends with the threads being configured for threading into bone. The body includes at least one through slot positioned between the opposing sides, with the through slot containing a biocompatible porous material for allowing the growth of bone through the slot of the body. The through slot is positioned between generally opposing sides of the body so as to provide contact between the biocompatible porous material and the end plates of the opposing vertebrae when the implant is inserted into at least one bore formed between the opposing vertebrae. Depending on the chosen material, the biocompatible porous material may also exhibit characteristics of osteoconductive or osteoinductive materials.

10 Claims, 3 Drawing Sheets

SPINAL FUSION DEVICE WITH POROUS MATERIAL

This application is a continuation-in-part of co-pending U.S. application Ser. No. 08/585,526 filed Jan. 16, 1996.

FIELD OF THE INVENTION

The present invention relates to spinal fusion devices to be placed between opposing vertebrae of a spine and more specifically to solid spinal fusion devices for insertion into bores formed between opposing vertebrae of a spine, the device being constructed so as to allow bony attachment while maintaining a load-bearing strength in excess of loads required by the spine.

BACKGROUND OF THE INVENTION

In a human spine the intervertebral disc acts as a stabilizer and as a mechanism for force distribution between the vertebral bodies. When the intervertebral disc is not present, the intervertebral space collapses causing pain, abnormal joint mechanics and premature development of arthritic changes.

Methods of treating injured or diseased discs have included chemical disintegration procedures and surgical excision, often followed by bony fusion to prevent spinal collapse or instability. With disc excision, no significant regeneration of disc material occurs. Replacement of an injured disc in an otherwise healthy spine may prevent arthritic changes and may stabilize the spinal segments. In diseased spines, replacement of the disc may reduce the progression of the disease process and may provide pain relief. Several methods have been developed for providing stability, via internal fixation, for the purpose of improving the probability, rate, and time associated with spinal fusion.

Methods of achieving internal fixation include the use of rods, plates and interbody cages. Examples of interbody cages are found in U.S. Pat. Nos. 4,961,740, 5,015,247 and 5,425,772. The cages or fusion devices described in these patents have threaded hollow bodies, which allow for the packing of autologous bone gratis. Typically, interbody cages are filled with bone graft material, either autograft or allograft, in order to enhance long term fixation of the interbody cage via bone attachment to the opposing vertebral end plates through the cage. Bone grafting is associated with a statistical chance of post-operative complications. The exact nature of these complications is generally related to the source of the graft material, but includes harvest site pain and immunological responses. Bone used as graft implants is often removed from another portion of a patient's body, which is called an autograft. A significant advantage of using a patient's own bone is the avoidance of tissue rejection, but harvesting bone also has its shortcomings. There is a risk to the patient in having a second surgical procedure (bone harvesting) performed at a secondary site which can lead to infection or additional pain to the patient. Further, the bone harvesting site is weakened by the removal of the bone. Other options for a bone graft source is bone removed from cadavers, called allograft, or from an animal called zenograft. While these kinds of bone grafts relieve the patient of having a secondary surgical site as a possible source of infection or pain, this option carries a high incidence of graft rejection and an increased risk of the transmission of communicable diseases. Further, zenograft and allograph material are more slowly incorporated into a patient's body than autograft material.

Another spinal fusion device, described in U.S. Pat. No. 4,878,915, is a solid plug implant with roughened outer surfaces for receiving bone ingrowth in order to fuse the plugs in the intervertebral space. The roughened outer surface on this device allows for only attachment of the device through interdigitation of the bone with the roughened outer surface of the plug.

Accordingly, it is an object of this invention to provide a spinal fusion device for fusing adjacent vertebral bodies without the need to use bone graft material. Another object of the invention is to provide for internal fixation/stabilization of the vertebrae to be fused through the use of a solid threaded device which has indentations in its outer surface containing a biocompatible potentially osteoinductive or osteoconductive material that contacts the bony end plates of the vertebral bodies to be fused. Yet another object is to provide a spinal fusion device that does not require bone growth into a hollow center of the device in order to augment the threaded fixation mechanism on the outer surface of the fusion device. A further object of the invention is to provide a solid spinal fusion device that has a through slot filled with a porous material that will allow for a column of bone growth through the device.

SUMMARY OF THE INVENTION

The present invention provides an implant for insertion into at least one bore formed between opposing vertebrae of a spine where the vertebrae are separated by a space. The implant is a solid cylindrical body having a first and a second end, an outer surface, opposing sides and a longitudinal axis. The body has threads on a portion of the outer surface between the first and second ends with the threads being configured for threading into bone tissue. The body includes at least two indentations on its outer surface, with each indentation containing bone attachment material for the attachment of bone to the material within the indentations. Each of the indentations are positioned on generally opposing sides of the body so as to be in contact with the bony end plates of the vertebral bodies to be fused.

In an alternate embodiment, the body can include at least one through slot positioned between the opposing sides instead of the indentations. The slot contains a biocompatible potentially osteoinductive or osteoconductive porous material for allowing growth of bone through the slot in the body.

As will subsequently be described, the inventive implant provides a spinal fusion device that does not require bone graft material in order to provide long term fixation or to augment the threaded fixation mechanism of the fusion device.

BRIEF DESCRIPTION OF THE DRAWINGS

A better understanding of the invention can be obtained when the detailed description of the exemplary embodiments set forth below is reviewed in conjunction with the accompanying drawings, in which.

DETAILED DESCRIPTION OF PREFERRED EMBODIMENT

The human spine is composed of a column of vertebrae and their joining structures. The vertebrae V are connected by intervertebral discs, which are positioned between opposing faces of adjacent vertebral bodies VB. Each vertebral body VB has an end plate E that is adjacent to the connecting intervertebral disc. When problems with the spine occur, surgery may be required to correct the problem and in one such procedure called a discectomy, the involved vertebral bodies are exposed and all or a part of the intervertebral disc is removed. A second procedure, termed a spinal fusion, may then be required to fuse the vertebral bodies together in order to prevent movement and to maintain the space originally occupied by the intervertebral disc. In some cases, one or two spinal fusion devices are inserted into the intervertebral space during a spinal fusion procedure following a discectomy.

Figure 1:
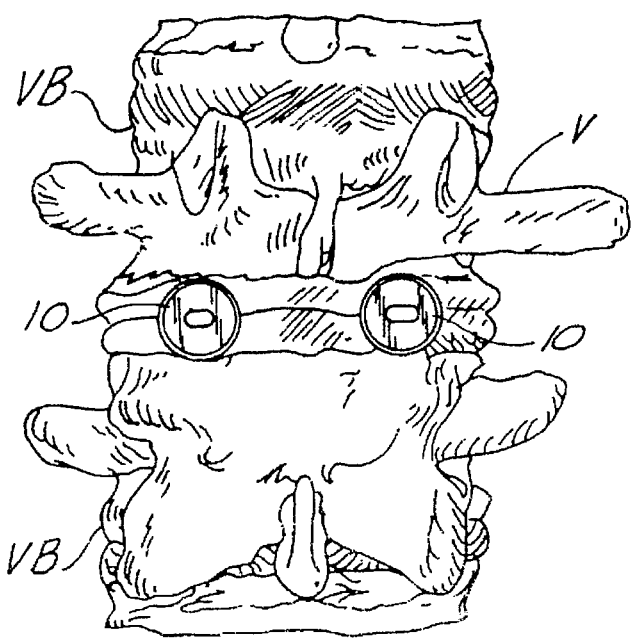
FIG. 1 is a schematic posterior plan view of a portion of human vertebrae with an implanted spinal fusion device of the present invention.
Figure 2:
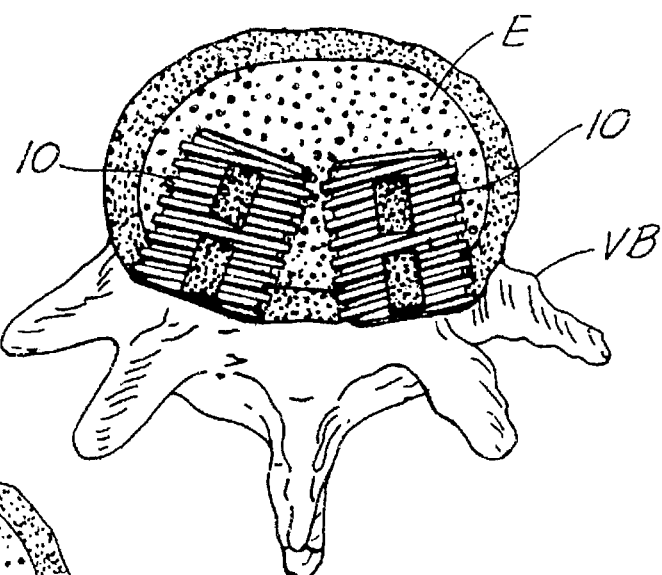
FIG. 2 is a schematic top view of a human vertebrae with two posteriorly implanted fusion devices of the present invention.
Figure 3:
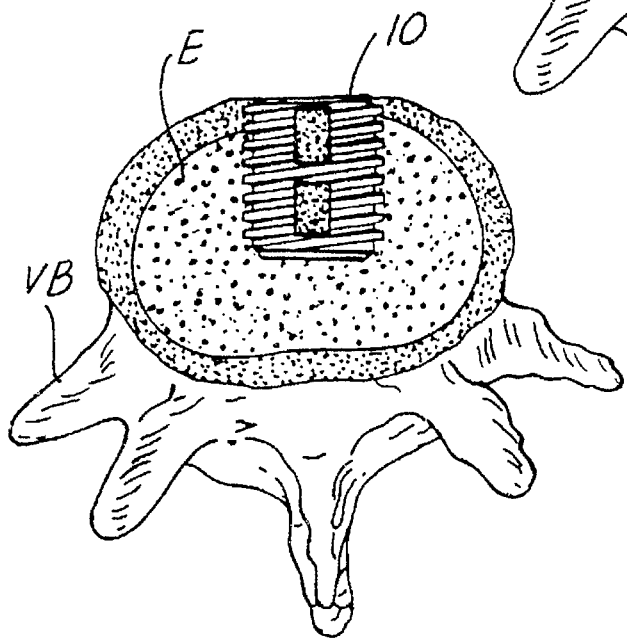
FIG. 3 is a schematic top plan view of a human vertebrae showing an anteriorly implanted fusion device of the present invention.
Figure 4:
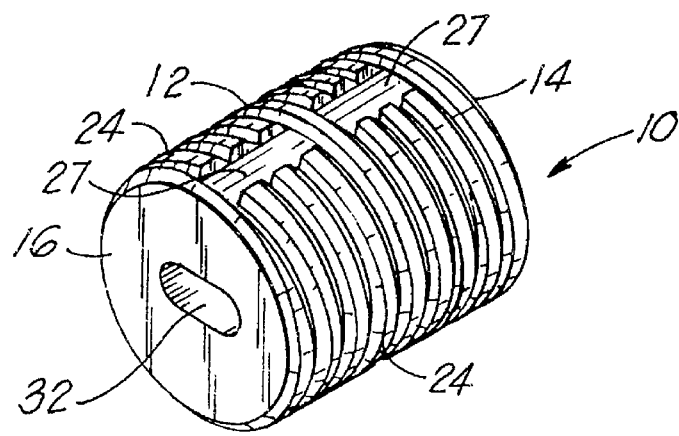
FIG. 4 is a perspective view of the present invention.
Figure 5:
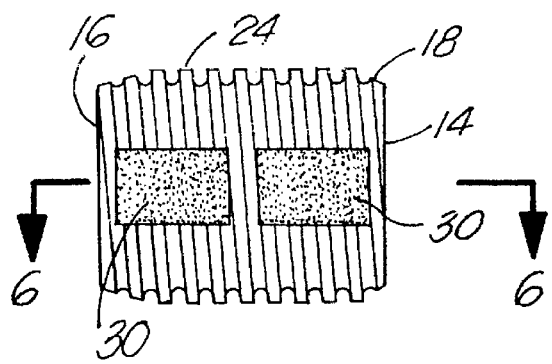
FIG. 5 is a top plan view of the fusion device of FIG. 4.
Figure 7:
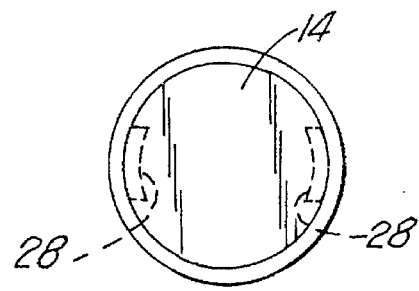
FIG. 7 is a plan view of a first end of the fusion device of FIG. 4.
Figure 6:
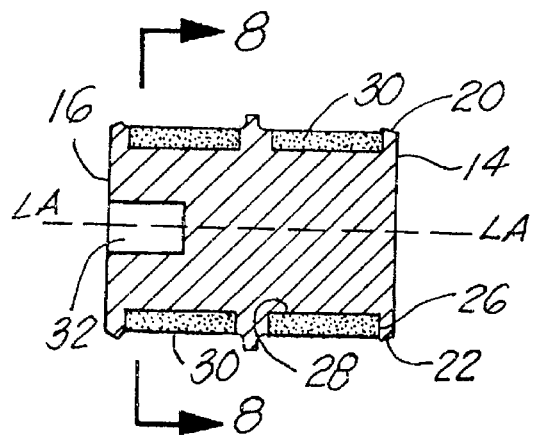
FIG. 6 is a cross-sectional view of the fusion device of FIG. 5.

FIGS. 1 and 2 illustrate vertebral bodies VB in which a fusion device or implant 10 of the present invention has been inserted into each bore formed between the posterior portion of opposing vertebral bodies VB of a spine. Alternatively, one or more fusion device or implant 10 may be inserted between an anterior portion of opposing vertebral bodies VB of a spine, as illustrated in FIG. 3. As shown in FIGS. 4, 5 and 6, the fusion device 10 of the present invention is in the shape of a solid generally cylindrical body 12 which has a first or leading end 14 and a second or trailing end 16. Body 12 includes an outer surface 18 and opposing sides 20, 22. Threading 24 is on a portion of the outer surface 18 of the body 12 between the first and second ends 14, 16. Preferably, the threading 24 is a cancellous type bone thread with buttressing on one side of the threading 24 which resists body 12 from backing out of the bore. Threading 24 is spirally wound around and is integral with the body 12. Body 12 also includes at least two indentations 26 on its outer surface 18 positioned along the longitudinal axis LA on generally opposing sides 20, 22 of the body 12. Indentations 26 have a surface 28 and in a preferred embodiment are generally about 0.25 to 3.0 mm deep. Each indentation 26 contains a bone attachment material 27 which allows for the attachment of bone to the material 27 contained within the indentations 26. In a preferred embodiment, the indentations 26 are generally rectangular in shape. Preferably, indentations 26 are positioned such that two indentations 26 are placed end-to-end along the longitudinal axis LA of each opposing side 20, 22 of the body 12 for a total of four indentations 26. However, indentations 26 can be positioned such that one rectangular indentation 26 that is generally the length of the body 12 is placed long the longitudinal axis LA of each opposing side 20, 22 of the body 12. This placement of indentations 26 provides for contact between the bone attachment material 27 and the end plates E of the opposing vertebral bodies VB when implant 10 is inserted into at least one bore formed between the opposing vertebral bodies VB as illustrated in FIGS. 2 and 3.

In one embodiment of the fusion device 10, the bone attachment material 27 includes an insert 30 formed from a biocompatible potentially osteoinductive or osteoconductive, porous, material. The porous material can include metallics, ceramics, polymers and composite materials. In a preferred embodiment the ceramic material is a calcium phosphate such as a calcium hydroxylapatite. In another embodiment of the fusion device 10, the bone attachment material 27 includes a metallic porous coating (not shown) on the surfaces 28 of the indentations 26. Insert 30 can also be formed from an inductive material such as BMP which may be combined with or carded by bioabsorbable polymer(s). An osteoconductive material such as calcium hydroxylapatite enhances bone growth in areas where bone tissue is normally found. An inductive material such as BMP which may be combined with bioabsorbable polymer(s) stimulates bone formation where bone tissue is not likely to be found.

Figure 8:
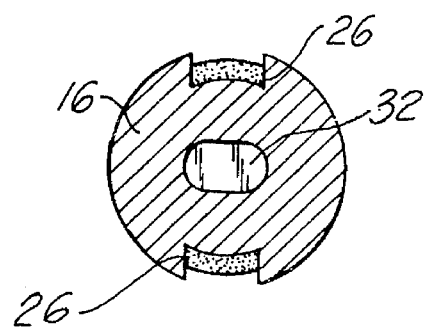
FIG. 8 is a plan view of a second end of the fusion device of FIG. 4.

Fusion device 10 also includes a centrally located internal opening 32 at the second end 16 of the body 12, as illustrated in FIGS. 4, 6 and 8. The centrally located internal opening 32 is configured to receive a tool receiving and mounting device (not shown) for securing the body 12 to a tool, such as a screwdriver, used to insert the implant 10 into at least one bore formed between opposing vertebral bodies VB of a spine.

Fusion device 10 can be implanted in either the anterior or posterior portion of a vertebrae V and either one or two fusion devices 10 may be used to provide for internal fixation and stabilization of the vertebrae V during a surgical procedure to fuse adjoining vertebral bodies (FIGS. 2 and 3). Inserts 30 can be formed from an osteoconductive or osteoinductive material and the solid cylindrical body 12 is preferably formed from an implantable grade material such as metals, ceramics, polymers or composites. Long term, the bone attachment material 27 in the indentations 26 obliviates the need for bone graft material as the bone tissue of the end plates E will become fixed directly to the bone attachment material 27. Threading 24 on the outer surface 18 of the body 12 provides initial attachment to the vertebral bodies against the natural shear forces placed on the spine. Without the initial attachment providing by the threading 24, it is possible for these shear forces to cause micromotion at the bone/bone attachment material 27 interface. This micromotion tends to reduce the integration of the bone attachment material 27 to the vertebral end plates E.

Figure 9:
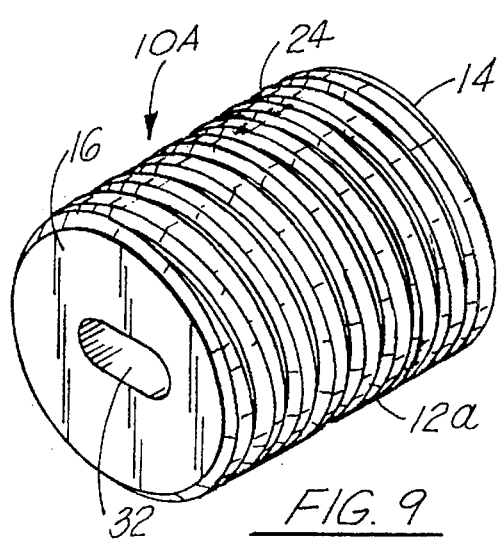
FIG. 9 is a perspective view of an alternate embodiment of the present invention.
Figure 13:
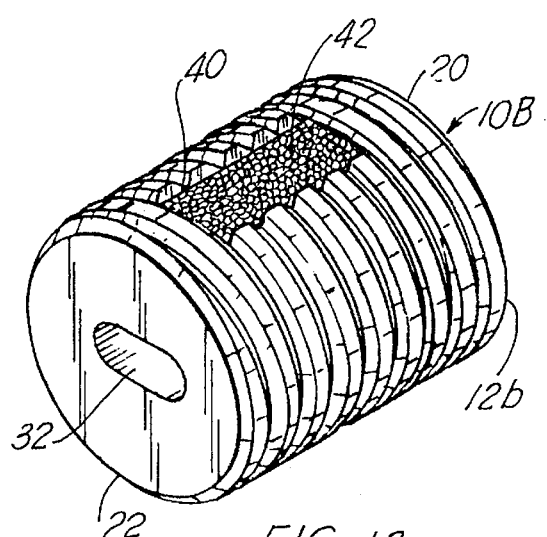
FIG. 13 is a perspective view of the fusion device of FIG. 10.
Figure 10:
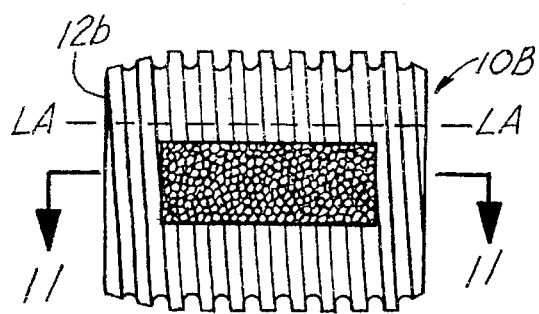
FIG. 10 is a top plan view of an alternate embodiment of the present invention.
Figure 11:
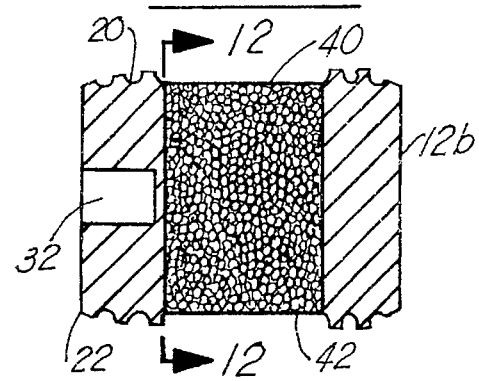
FIG. 11 is a cross-sectional view of the fusion device of FIG. 10.

In an alternate embodiment, as shown in FIG. 9, fusion device 10A has a solid cylindrical body 12a formed from a biocompatible osteoconductive material such as bioactive hydroxyapatite-polymer composites. Body 12a is preferably composed of a hydroxylapatite (HA) reinforced polyethylene composite. Cortical bone at the ultra-structural level is a hydroxylapatite reinforced collagen composite. Thus, the equivalence of microstructure and deformation behavior give hydroxylapatite-polyethylene composites a special property as a bone analogue material. HA reinforced polyethylene composites offer the potential of a stable implant-tissue interface during physiological loading. In addition to the ability to tailor-make the composition of the composite as the mean particle size and the particle size distribution, as well as the surface area, of the HA can be varied, so as to produce different mechanical properties. The body 12a has a first and a second end 14, 16, opposing sides 20, 22 and an outer surface 18. Threading 24 is on a portion of the outer surface 18 between the first and second ends 14, 16. When the implant 10A is inserted into at least one bore formed between the opposing vertebral bodies VB, the opposing sides 20, 22 contact the end plates E of the opposing vertebral bodies VB so as to allow the bone tissue of the end plates E to chemically bond directly to the outer surface 18 of the body 12a. The implant 10A also includes an internal opening 32 configured to receive a tool receiving and mounting device such as a screwdriver used for inserting the implant 10A into at least one bore formed between opposing vertebrae of the spine.

Figure 12:
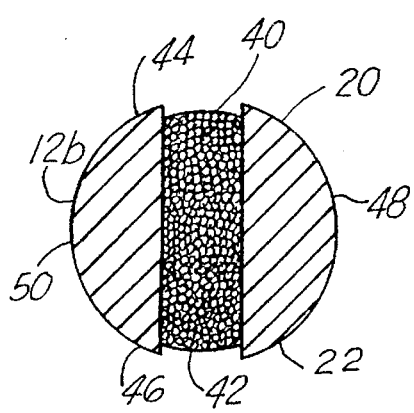
FIG. 12 is a cross-sectional view of the fusion device of FIG. 11.

In a second alternate embodiment as shown in FIGS. 10–14, a spinal fusion device 10B has a body 12b with a through slot 40 instead of the indentations 26. However, body 12b includes all of the other features of body 12. Slot 40 is a continuous through slot positioned between the opposing sides 20, 22 of body 12b and is placed along the longitudinal axis LA. Body 12b can include at least one through slot 40 or two through slots 40 that are positioned in the generally same location as the indentations 26 of the fusion device 10. As illustrated in FIG. 12, body 12b includes a top portion 44 on the opposing side 20 and a parallel bottom portion 46 on the second opposing side 22. Two parallel side walls 48, 50 extend between the top and bottom portion 44, 46 of body 12b. Side walls 48, 50 are positioned along the longitudinal axis LA of the body 12b. Preferably, the through slot 40 is generally rectangular in shape and is positioned between the top portion 44 and the bottom portion 46 of the opposing walls 20, 22 of the body 12b.

The through slot 40 is filled with a biocompatible potentially osteoinductive or osteoconductive, porous, material 42. The porous material 42 can include metallies, ceramics, polymers and composite materials. In a preferred embodiment the ceramic material is a calcium phosphate such as a calcium hydroxylapatite. Alternatively, an inductive material such as BMP which may be combined with bioabsorbable polymer(s) can be used to fill the slot 40. The through slot 40, positioned between the opposing sides 20, 22 of the body 12b, provides contact between the biocompatible porous material 42 and the end plates E of the opposing vertebrae VB when the implant is inserted into at least one bore formed between the opposing vertebrae of the spine. In this position within the bore, the biocompatible porous material 42 allows for a column of bone to be generated through the spinal fusion device 10B.

Figure 14:
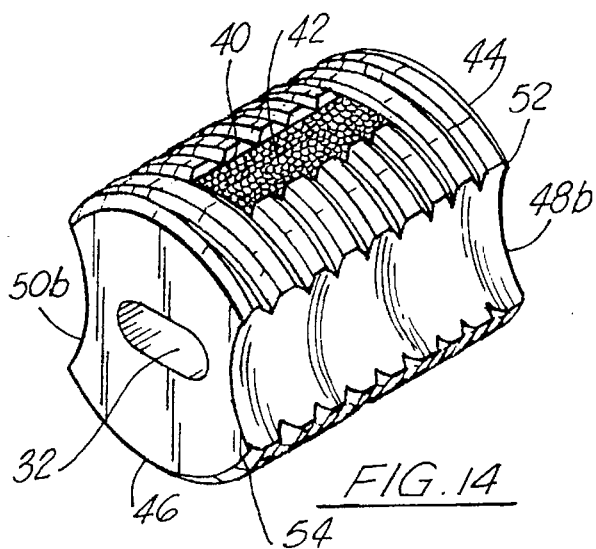
FIG. 14 is a perspective view of an alternate embodiment of the present invention.

In certain surgical situations, it would be desirous to have a spinal fusion device that can be "nested" closely with a cylindrical spinal fusion device such as fusion device 10 or 10A. For these situations, the spinal fusion device of the subject invention can be formed in which the two side walls 48, 50 are concave in shape along the longitudinal axis LA of the body 12b, as shown in FIG. 14. The concave side walls 48b, 50b are joined to the arcuate portion of the top and bottom portions 44, 46 at junction 52 of the top portion 44 and at junction 54 of the bottom portion 46. The concave side walls 48b, 50b allow the fusion device 10B to be nested with another fusion device 10B or the fusion device 10 or 10A in which all have the same effective diameters. Nesting of fusion devices allows for the use of taller fusion devices when a patient's vertebral disc width will not accommodate two fusion devices plus the at least 4 mm required space between the two implanted fusion devices.

It will be appreciated that implant 10, 10A and 10B are intended for use in a wide variety of vertebral body sizes and the dimensions of the implant 10, 10A and 10B will vary necessarily with the size of the vertebral body in which the implant 10, 10A and 10B is to be used. Making variations to the dimensions and sizes of the implant 10, 10A and 10B in order to accommodate differing sizes of vertebral bodies will be well within the skill of the art. Generally, however, the diameter of implant 10, 10A and 10B can be between about 6 to 20 mm and the length between about 8 to 30 mm.

Although the present invention has been described with reference to its preferred embodiments, those skilled in the art will recognize changes which may be made in form or structure which do not depart from the spirit of the invention already described in the Specification and embodied in the claims which follow.

What is claimed is:

1. An implant for insertion into at least one bore formed between opposing vertebrae of a spine where the vertebrae are separated by a space and each vertebrae has end plates, the implant comprising:

a) a solid generally cylindrical body having a first and a second end, an outer surface, opposing sides and a longitudinal axis;

b) the body having threads on a portion of the outer surface between the first and second ends, the threads configured for threading into bone;

c) the body including at least one through slot positioned between the opposing sides, the through slot containing a biocompatible porous material for allowing the growth of bone through the slot; and d) the through slot being positioned between generally opposing sides of the body so as to provide contact between the biocompatible porous material and the end plates of the opposing vertebrae when the implant is inserted into at least one bore formed between the opposing vertebrae.

2. The implant of claim 1, wherein the body includes two generally rectangular through slots.

3. The implant of claim 1, wherein the porous material is selected from a group consisting of biocompatible metallics, ceramics, polymers, and composite materials.

4. The implant of claim 3, wherein the ceramic material is a calcium phosphate.

5. The implant of claim 4, wherein the calcium phosphate is a calcium hydroxylapatite.

6. The implant of claim 1, wherein the biocompatible porous material includes an osteoinductive material such as BMP.

7. The implant of claim 1, wherein two implants are inserted into two bores formed between opposing vertebrae of a spine.

8. The implant of claim 1, wherein the second end of the body has a centrally located internal opening configured to receive a tool receiving and mounting device for securing the body to a tool for inserting the implant into at least one bore formed between opposing vertebrae of a spine.

9. The implant of claim 1, wherein the opposing sides of the body include a top portion on one opposing side and a parallel bottom portion on a second opposing side with two parallel side walls extending between the top and bottom portions, the top and bottom portions and the two parallel side walls being positioned along the longitudinal axis of the body.

10. The implant of claim 9, wherein the top and bottom portions are arcuate in shape conforming to the cylindrical shape of the body and the two side walls are concave in shape along the longitudinal axis of the body.

* * * * *